United States Patent [19]

Allgeier et al.

[11] 3,941,799

[45] Mar. 2, 1976

[54] 6-SUBSTITUTED-11B-PHENYL-3, 11BH-OXAZIRINO[2,3-D]-S-TRIAZOL[4,3-A][1,4]BENZODIAZEPINES

[75] Inventors: Hans Allgeier, Haagen, BD., Germany; Andre Gagneux, Basel, Switzerland

[73] Assignee: Ciba-Geigy Corporation, Ardsley, N.Y.

[22] Filed: May 16, 1973

[21] Appl. No.: 360,852

[30] Foreign Application Priority Data

May 18, 1972 Switzerland.......................... 7386/72

[52] U.S. Cl. ... 260/308 R; 204/158 R; 260/239 BD; 260/559 H; 260/561 H; 424/269
[51] Int. Cl.².................................... C07D 498/14
[58] Field of Search ............................... 260/308 R

[56] References Cited
UNITED STATES PATENTS 3,681,343  8/1972  Hester........................... 260/308 R Primary Examiner—Alton D. Rollins
Attorney, Agent, or Firm—Joseph G. Kolodny; John J. Maitner; Theodore O. Groeger

[57] ABSTRACT

Compounds of the class of 6-substituted 11b-phenyl-3,11b-oxazirino[2,3-d]-s-triazolo[4,3-a][1,4]benzodiazepines have valuable pharmacological properties and are active ingredients for therapeutic compositions. In particular, these new compounds have an anticonvulsive action and inhibit somatic reflexes. Specific embodiments are 10-chloro-11b-phenyl-3,11bH-oxazirino[2,3-d]-s-triazolo[4,3-a][1,4]benzodiazepine-6-methanol, 10-chloro-11b-phenyl-3,11bH-oxazirino[2,3-d]-s-triazolo[4,3-a][1,4]benzodiazepine-6-carboxaldehyde-diethylacetal and 10-chloro-11b-(o-chlorophenyl)-3,11bH-oxazirino[2,3-d]-s-triazolo[4,3-a][1,4]benzodiazepine-6-carboxaldehyde-diethylacetal.

6 Claims, No Drawings

6-SUBSTITUTED-11B-PHENYL-3, 11BH-OXAZIRINO[2,3-D]-S-TRIAZOL[4,3-A][1,4]BENZODIAZEPINES

The present invention relates to new diazepine derivatives, to a process for their production, to pharmaceutical preparations containing the new compounds, and to the use thereof.

The new diazepine derivatives correspond to the general formula I

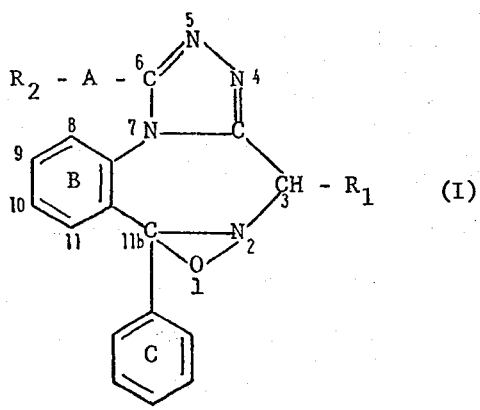

wherein
  $R_1$ represents hydrogen or an alkyl group having 1 to 3 carbon atoms,
  A represents an alkylene group having 1 to 3 carbon atoms,
  $R_2$ represents the hydroxyl group, a mono- or diarylmethoxy group, or
  $R_2$—A together represent a dialkoxymethyl group of which the alkoxy radicals contain 1 to 4 carbon atoms, or an alkylenedioxymethyl group having in all 3 to 6 carbon atoms, and
  the rings B and C can be substituted by halogen up to atomic number 35, trifluoromethyl, alkyl or alkoxy groups having 1 to 6 carbon atoms.

The invention relates likewise to the addition salts of the compounds of the general formula I in which compounds $R_2$ is an amino group, a polymethyleneimino group or a morpholino group, optionally substituted as defined, with inorganic and organic acids.

As an alkyl group in the compounds of the general formula I, $R_1$ is, for example, the methyl, ethyl or propyl group. By an alkylene group A is meant any desired bivalent, saturated aliphatic hydrocarbon radical having 1 to 3 carbon atoms, such as the methylene, ethylidene, 1-methylethylidene, ethylene, propylene or trimethylene groups; of particular importance among these groups is the methylene group.

As a monoarylmethoxy group, $R_2$ is, for example, the o-, m- or p-chlorobenzyloxy group, the o-, m- or p-methylbenzyloxy group, the o-, m- or p-methoxybenzyloxy group or the 3,4,5-trimethoxy-benzyloxy group, and particularly the benzyloxy group; and as a diarylmethoxy group, $R_2$ is, in particular, the diphenylmethoxy group.

$R_2$-A as a dialkoxymethyl group is, in particular, the dimethoxymethyl or diethoxymethyl group.

Halogen atoms as substituents of the rings B and C are fluorine, chlorine or bromine atoms, while alkyl groups or alkoxy groups having 1 to 6 carbon atoms are, for example, methyl, ethyl, propyl, isopropyl, butyl, isobutyl, tert.butyl, pentyl, isopentyl, 2,2-dimethylpropyl, hexyl or isohexyl groups; or methoxy, ethoxy, propoxy, isopropoxy, butoxy, isobutoxy, pentyloxy, isopentyloxy, 2,2-dimethylpropoxy, hexyloxy or isohexyloxy groups. A substituent of the ring B is especially in the 10-position, and is preferably fluorine, bromine, the trifluoromethyl group and, in particular, chlorine. The ring C is preferably unsubstituted, or substituted in any desired position by fluorine, chlorine or bromine, particularly by fluorine or chlorine in the o-position.

The compounds of the general formula I possess valuable pharmacological properties. They have a central depressant action, especially an anticonvulsive action; and they also inhibit somatic reflexes. The anticonvulsive effectiveness can be verified, for example, in the case of oral administration to the mouse in the electroshock test, in the psychomotor test and, in particular, in the strychnine convulsion test, as well as in the pentetrazole test. The stated properties and others, which can be determined by selected standard tests [cp. W. Theobald and H. A. Kunz, Arzneimittelforsch. 13, 122 (1963), as well as W. Theobald et al., Arzneimittelforsch. 17, 561 (1967)], distinguish the compounds of the general formula I as being suitable active substances for tranquillisers and anticonvulsants, which are applicable, for example, for the treatment of conditions of tension and agitation, as well as for the treatment of epilepsy.

Of particular importance are compounds of the general formula I having hydrogen as $R_1$, the methylene group as A and the benzyloxy or p-methoxybenzyloxy group and, in particular, the hydroxyl group as $R_2$; and among these compounds particularly those having a chlorine atom in ring B in the 10-position and ring C unsubstituted or substituted in the o-position by fluorine or especially chlorine. Also of particular importance are compounds of the general formula I in which $R_2$—A together represent the dimethoxymethyl group, and particularly the diethoxymethyl group, while $R_1$ represents hydrogen, and the rings B and C have the aforementioned preferred substitution characteristics.

The compounds of the general formula I are produced according to the invention by a process in which light is allowed to act on a compound of the general formula II

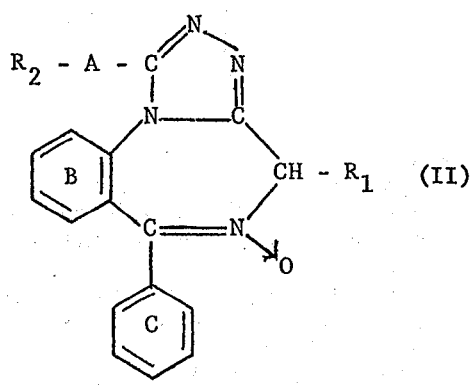

wherein $R_1$, $R_2$ and A have the meanings given under formula I, and rings B and C can be substituted as defined there; and, optionally, a reaction product of the general formula I wherein $R_2$ is a mono- or diarylmethoxy group split to form the corresponding compound in which $R_2$ is a hydroxyl group.

Daylight can be used for the production of small amounts of compounds of the general formula I. For larger amounts it is possible to employ the usual sources of light, such as normal filament lamps; also, for example, mercury vapour lamps having a main wave band of 300 to 400 m$\mu$, i.e. high-pressure lamps or medium-pressure lamps, these having a Pyrex-glass filter for the elimination of the rays below ca. 300 m$\mu$ which would decompose the compounds of the general formula I. The solvents used are inert organic solvents; for example, ethereal liquids, particularly tetrahydrofuran, also esters, ketones, hydrocarbons or chlorinated hydrocarbons. The irradiation is performed preferably with the exclusion of oxygen; for example, under nitrogen or under an inert gas such as argon or helium. The reaction temperature can vary within a wide range, i.e. between ca. $-70°$ C and $+150°$ C; it is however preferably between ca. $=10°$ C and $+30°$ C.

The 5-oxides of the general formula II which are required as starting materials are preferably produced from the corresponding compounds, not oxidised in the 5-position, by treatment with hydrogen peroxide or peroxy acids at a temperature of ca. $0°$ to $70°$ C. Suitable peroxy acids are, for example, peroxyacetic acid or peroxybenzoic acids, such as peroxybenzoic acid and particularly m-chloro-peroxybenzoic acid. The oxidising agents are preferably used in a solvent, e.g. peroxyacetic acid in acetic acid, and the peroxybenzoic acids in halogenated hydrocarbons such as methylene chloride or chloroform. The compounds not oxidised in the 5-position which are required as intermediates are for their part new substances. The starting materials from which they are produced are, e.g., compounds of the general formula III

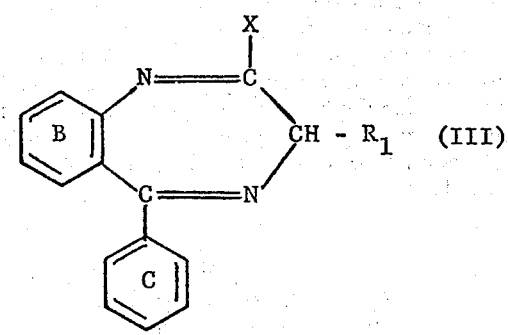

wherein
X represents a mercapto group, a lower alkoxy or alkylthio group optionally activated by a substituent, or an optionally mono- or disubstituted amino group,
$R_1$ has the meaning given under formula I, and the rings B and C can be substituted as defined under formula I. X is preferably a methylthio, mercapto, methoxy, amino, methylamino, benzylamino or dimethylamino group; and as an alkoxy or alkylthio group activated by a substituent it is, for example, the o- or p-nitrobenzyloxy group or the o- or p-nitrobenzylthio group.

The compounds of the general formula III defined above are reacted with acid hydrazides of the general formula IV

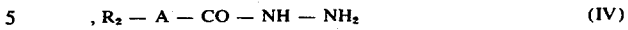

wherein $R_2$ and A have the meanings given under formula I; and, optionally, an obtained product of which the radical $R_2$ is a monoarylmethoxy or diarylmethoxy group split to form a corresponding compound of which the radical $R_2$ is the hydroxyl group.

The reaction according to the process is performed preferably at a reaction temperature of ca. $80°$ to $180°$ C in an inert solvent. Suitable inert solvents are, for example, hydrocarbons such as toluene or xylene, halogenated hydrocarbons such as chlorobenzene, ethereal liquids such as diethylene glycol dimethyl ether, diethylene glycol diethyl ether or dioxane, amides, particularly N,N,N',N', N'',N''-hexamethyl-phosphoric acid triamide or N,N-dimethylacetamide, sulphoxides such as dimethylsulphoxide, and alcohols such as N-butanol. The reaction times are preferably between ca. 1 and 24 hours.

Compounds embraced by the general formula III are described in the literature; see inter alia L. H. Sternbach and E. Reeder, J.Org.Chem. 26, 1111 (1961), S. C. Bell et al., J.Med.Chem. 5, 63 (1962), G. A. Archer and L. H. Sternbach, J.Org.Chem 29, 231 (1964) and J. Farber et al., J.Med.Chem. 7, 235 (1964). Also described are compounds embraced by the general formula IV, such as 2-benzyloxy-acetic acid hydrazide and glycolic acid hydrazide [cp. Th. Curtius and N. Schwan, J.prakt. Chem. [2] 51, 364 (1895)], as well as dimethoxyacetic acid hydrazide (cp. E. J. Browne and J. B. Polya, J.Chem. Soc. 1962, 5149). Further compounds of the general formulae III and IV can be produced analogously to the known compounds The optionally performed splitting of compounds of the general formula I or II of which the radical $R_2$ is a monoarylmethoxy or diarylmethoxy group to form corresponding compounds of which the radical $R_2$ is the hydroxyl group is preferably performed with the aid of hydrohalic acids such as hydrochloric acid, hydriodic acid or, in particular, hydrobromic acid. It is advantageous to use the hydrohalic acids in a solvent. Suitable solvents are carboxylic acids such as acetic acid. The reaction temperature is ca. $20°$ to $150°$ C. Compounds which can be split particularly well are compounds in which $R_2$ is a p-methoxybenzyloxy group.

The present invention relates also to modifications of the aforementioned process and of the consequent reaction mentioned subsequent to this, as well as of the preceding steps, whereby a process is interrupted at some stage, or whereby a compound occurring at some particular stage is taken as the starting material and the uncompleted steps performed, or whereby a starting material is formed under the reaction conditions, or is optionally used in the form of a salt.

The new active substances are administered orally, rectally or parenterally. The dosage amount depends on the mode of administration, on the species, on the age and on the individual condition. The daily doses of compounds of the general formula I vary between 0.02 mg/kg and 2 mg/kg for warm-blooded animals. Suitable dosage units, such as dragees, tablets, suppositories or ampoules, preferably contain 0.5 – 25 mg of an active substance according to the invention.

Dosage units for oral administration contain as active substance preferably between 1 and 50% of a compound of the general formula I. They are produced by the combination of the active substance with, for example, pulverulent carriers such as lactose, saccharose, sorbitol or mannitol; starches such as potato starch, maize starch or amylopectin, also laminaria powder or citrus pulp powder; cellulose derivatives or gelatine, optionally with the addition of lubricants such as magnesium or calcium stearate or polyethylene glycols, to form tablets or dragee cores. The dragee cores are coated, for example, with concentrated sugar solutions, which may also contain, for example, gum arabic, talcum and/or titanium dioxide; or with a lacquer dissolved in readily volatile organic solvents or solvent mixtures. Dyestuffs can be added to these coatings in order, for example, to facilitate identification of the various doses of active substance.

Further suitable oral dosage units are hard capsules made from gelatine, as well as soft closed capsules made from gelatine and a softener such as glycerin. The hard capsules contain the active substance preferably as a granulate, e.g. in admixture with fillers such as maize starch, and/or lubricants such as talcum or magnesium stearate, and optionally stabilisers such as sodium metabisulphite ($Na_2S_2O_5$) or ascorbic acid. In soft capsules, the active substance is preferably dissolved or suspended in suitable liquids such as liquid polyethylene glycols, to which likewise stabilisers may be added.

Suitable dosage units for rectal administration are, for example, suppositories consisting of a combination of an active substance with a suppository foundation substance. Applicable suppository foundation substances are, for example, synthetic triglycerides, paraffin hydrocarbons, polyethylene glycols or higher alkanols. Likewise suitable for the said purpose are hard gelatine capsules consisting of a combination of the active substance with a foundation substance. Suitable foundation substances are, for example, liquid triglycerides, polyethylene glycols or paraffin hydrocarbons.

Ampoules for parenteral administration, particularly intramuscular administration, preferably contain an aqueous dispersion of an active substance of the general formula I in a concentration preferably of 0.1 – 1%, optionally together with suitable stabilisers and buffer substances.

The following directions serve to further illustrate the preparation of tablets, dragees, capsules and suppositories.

a. An amount of 50 g of 10-chloro-11b-phenyl-3,11bH-oxazirino [2,3-a]-s-triazolo[4,3-a][1,4]benzodiazepine-6-methanol is mixed with 175.80 g of lactose and 169.70 g of potato starch; the mixture is moistened with an alcoholic solution of 10 g of stearic acid and then granulated through a sieve. After the drying of the granulate, 160 g of potato starch, 200 g of talcum, 2.50 g of magnesium stearate and 32 g of colloidal silicon dioxide are mixed in; the mixture is pressed to form 10,000 tablets each weighing 80 mg and each containing 5 mg of active substance; these can be optionally provided with grooves to allow a more precise adjustment of the dosage amount.

b. A granulate is produced from 50 g of 10-chloro-11b-phenyl-3,11bH-oxazirino[2,3-d]-s-triazolo[4,3-a][1,4]benzodiazepine-6-carboxaldehyde-diethylacetal, 175.90 g of lactose and the alcoholic solution of 10 g of stearic acid; the granulate, after drying, is mixed with 56.60 g of colloidal silicon dioxide, 165 g of talcum, 20 g of potato starch and 2.50 g of magnesium stearate; the whole is subsequently pressed out to form 10,000 dragee cores. These are afterwards coated with a concentrated syrup made from 502.28 g of crystallised saccharose, 6 g of shellac, 10 g of gum arabic, 0.22 g of dyestuff and 1.5 g of titanium dioxide, and finally dried. The obtained dragees each weigh 100 mg and each contain 5 mg of active substance.

c. In order to produce 1000 capsules each containing 5 mg of active substance, 5 g of 10-chloro-11b-phenyl-3,11bH-oxazirino[2,3-d]-s-triazolo[4,3-a][1,4]benzodiazepine-6-methanol is mixed with 268 g of lactose; the mixture is evenly moistened with an aqueous solution of 2 g of gelatine, and then granulated through a suitable sieve (e.g. sieve III according to Ph.Helv. V). The granulate is mixed with 10.0 g of dried maize starch and 15.0 g of talcum, and the mixture uniformly filled into 1000 hard gelatine capsules, size 1.

d. A suppository mixture is prepared from 1.0 g of 10-chloro-11b-phenyl-3,11bH-oxazirino[2,3-d]-s-triazolo [4,3-a [1,4]benzodiazepine-6-carboxaldehyde-diethylacetal and 169.0 g of adeps solidus; the mixture is used to pour 100 suppositories each containing 10 mg of active substance.

As the active substance for tablets, dragees and capsules, it is also possible to use, for example, the 0.4-fold amounts of 10-chloro-11b-(o-chlorophenyl)- 3,11bH-oxazirino[2,3-d]-s-triazolo[4,3-a][1,4]benzodiazepine-6-carboxaldehyde-diethylacetal.

The following examples further illustrate the production of new compounds of the general formula I and of intermediates not hitherto described; the examples do not, however, in any way limit the scope of the invention. Temperatures are in degrees Centigrade. The petroleum ether used is always one having a boiling range of 40°–65° C.

EXAMPLE 1

A solution of 0.6 g of 6-phenyl-8-chloro-4H-s-triazolo[4,3-a][1,4]benzodiazepine-1-methanol-5-oxide in 60 ml of tetrahydrofuran is allowed to stand in a closed flask for 10 days in daylight. The solution is afterwards concentrated by evaporation. The oily residue is chromatographed in ethyl acetate/methanol (9:1) on silica gel. The eluted crude reaction product is recrystallised from tetrahydrofuran/petroleum ether to obtain 10-chloro-11b-phenyl-3,11bH-oxazirino[2,3-d]-s-triazolo[4,3-a][1,4]benzodiazepine-6-methanol, M.P. 167°–169°.

The following are obtained in an analogous manner with the use of the same amount of starting material:
from 1-(benzyloxymethyl)-6-phenyl-8-chloro-4H-s-triazolo [4,3-a][1,4]benzodiazepine-5-oxide:- 6-(benzyloxymethyl)- 10-chloro-11-b-phenyl-3,11bH-oxazirino[2,3-d]-s-triazolo [4,3-a][1,4]benzodiazepine;
from 6-(o-chlorophenyl)-8-chloro-4H-s-triazolo[4,3-a][1,4]benzodiazepine-1-methanol-5-oxide:- 10-chloro-11b-(o-chlorophenyl)-3,11bH-oxazirino[2,3-d]-s-triazolo (4,3-a][1,4]benzodiazepine-6-methanol, and from 1-[p-methoxybenzyloxy)-methyl]-6-(o-chlorophenyl)-8-chloro-4H-s-triazolo[4,3-a][1,4]benzodiazepine-5-oxide:-6- [(p-methoxybenzyloxy)-methyl]-10-chloro-11-b-(o-chlorophenyl)-3,11bH-oxazirino[2,3-d]-s-triazolo[4,3-a][1,4]benzodiazepine.

The 5-oxides required as starting materials are produced as follows:

a. A solution of 30 g of 2-(methylthio)-5-phenyl-7-chloro-3H-1,4-benzodiazepine [cp. G. A. Archer et al., J.Org. Chem. 29, 231 (1964)] and 19.8 g of 2-benzyloxyacetic acid hydrazide [cp. Th. Curtius N. Schwan, J.prakt.Chem. [2] 51, 353 (1895)] in 160 ml of hexamethylphosphoric acid triamide is heated for 8 hours at 140°. The solvent is then distilled off in vacuo and the residue distributed between methylene chloride and water. The organic phase is separated, washed with saturated aqueous sodium chloride solution, dried over sodium sulphate and concentrated by evaporation. 1-(Benzyloxymethyl) -6-phenyl-8-chloro-4H-s-triazolo[4,3-a][1,4]benzodiazepine crystallises out; it melts at 163°–165°.

The compound 1-[p-methoxybenzyloxy)-methyl]-6-(o-chlorophenyl)-8-chloro-4H-s-triazolo[4,3-a][1,4]benzodiazepine, M.P. 200°–203° (from ethyl acetate) is produced in an analogous manner by reaction of 33.4 g of 2-(methyl-thio)-5-(o-chlorophenyl)-7-chloro-3H-1,4-benzodiazepine [obtainable from the corresponding 2-oxo compound (described in J.Org.Chem. 27, 3988 (1962)) by conversion into the corresponding 2-thion, and methylation of the latter with dimethyl sulphate in methanolic sodium hydroxide solution, analogously to the process described in J.Org. Chem. 29, 231 (1964)] with 33.0 g of 2-(p-methoxybenzyloxy)-acetic acid hydrazide [obtainable by reaction of 58 g of 2-(p-methoxybenzyloxy)-acetic acid methyl ester (described in Compt.rend. 237, 1162 (1953)) with 22.7 g of hydrazine hydrate in ethanolic solution for 3 days at 25°].

b. An amount of 25 g of 1-(benzyloxymethyl)-6-phenyl-8-chloro-4H-s-triazolo[4,3-a][1,4]benzodiazepine is dissolved in 200 ml of glacial acetic acid; there is then added to the solution 170 ml of 48% aqueous hydrobromic acid. The mixture is heated for 90 minutes at 80° and then cooled to 5°; while stirring is maintained, the mixture is adjusted to pH 6 with concentrated sodium hydroxide solution, and water as well as methylene chloride subsequently added. The organic phase is separated, washed with saturated aqueous sodium chloride solution, dried over sodium sulphate and concentrated by evaporation. The residue is dissolved in ethyl acetate/methanol (9:1); the solution is filtered through a column of 150 g of silica gel (Merck, particle size 0.05 – 0.2 mm), and the column eluted with ethyl acetate/methanol (9:1) to (7:3). The eluate is concentrated by evaporation and the residue crystallised from ethyl acetate/ether to obtain 6-phenyl-8-chloro-4H-s-triazolo[4,3-a][1,4]benzodiazepine-1-methanol, M.P. 210°–211°.

c. An amount of 72 ml of 48% aqueous hydrobromic acid is added to 20° to a solution of 9.7 g of 1-[(p-methoxybenzyloxy)-methyl]-6-(o-chlorophenyl)-8-chloro-4H-s-triazolo[4,3-a][1,4]benzodiazepine in 90 ml of glacial acetic acid. The reaction mixture is stirred for 55 minutes; it is then neutralised with 30% sodium hydroxide solution and extracted with methylene chloride. The organic phase is separated, washed with water, dried over sodium sulphate and concentrated by evaporation. Crystallisation of the residue from ethyl acetate/petroleum ether yields 6-(o-chlorophenyl)-8-chloro-4h-s-triazolo[4,3-a][1,4]benzodiazepine-1-methanol, M.P. 235°–237°.

d. A solution of 3.11 g of m-chloroperbenzoic acid in 40 ml of methylene chloride is added dropwise in the course of 10 minutes at 0°–5°, with stirring, to a solution of 3.0 g of 6-phenyl-8-chloro-4H-s-triazolo[4,3-a][1,4]benzodiazepine-1-methanol in 80 ml of methylene chloride. In an ice bath being allowed to melt, the reaction mixture is stirred for a further 16 hours; it is subsequently concentrated in vacuo, and ether and petroleum ether are then added. The precipitated crystals are filtered with suction, and recrystallised twice from methanol/ethyl acetate/ether. The obtained 6-phenyl-8-chloro-4H-s-triazolo[4,3-a][1,4]benzodiazepine-1-methanol-5-oxide melts at 267°–269°.

The following are obtained in an analogous manner: starting with 3.84 g of 1-(benzyloxymethyl)-6-phenyl-8-chloro-4H-s-triazolo[4,3-a][1,4]benzodiazepine:- 1-(benzyloxymethyl)-6-phenyl-8-chloro-4H-s-triazolo[4,3-a][1,4]benzodiazepine-5-oxide, M.P. 189°–193° (from ether);

starting with 3.30 g of 6-(o-chlorophenyl)-8-chloro-4H-s-triazolo[4,3-a][1,4]benzodiazepine-1-methanol:- 6-(o-chlorophenyl)-8-chloro-4H-s-triazolo[4,3-a][1,4]benzodiazepine-1-methanol-5-oxide; and starting with 3.95 g of 1-[(p-methoxybenzyloxy)-methyl]-6-(o-chlorophenyl)-8-chloro-4H-s-triazolo[4,3-a][1,4]benzodiazepine:- 1-[(p-methoxybenzyloxy)-methyl]-6-(o-chlorophenyl)-8-chloro-4H-s-triazolo[4,3-a][1,4]benzodiazepine-5-oxide.

EXAMPLE 2

A solution of 0.6 g of 6-phenyl-8-chloro-4H-s-triazolo[4,3-a][1,4]benzodiazepine-1-carboxaldehyde-diethylacetal-5-oxide in 60 ml of tetrahydrofuran is allowed to stand in a closed flask for 6 days in daylight. The solution is afterwards concentrated by evaporation to 20 ml; petroleum ether is then added. 10-Chloro-11b-phenyl-3,11bH-oxazirino[2,3-d]-s-triazolo[4-,3a][1,4]benzodiazepine-6-carboxaldehyde-diethylacetal crystallises out and is filtered off, M.P. 136°–137°.

IN an analogous manner there is obtained, with the use of the same amount of 6-phenyl-8-chloro-4H-s-triazolo [4,3-a][1,4]benzodiazepine-1-carboxaldehyde-dimethylacetal-5-oxide:-10-chloro-11b-phenyl-3,11bH-oxazirino [2,3-d]-s-triazolo[4,3-a][1,4]benzodiazepine-6-carboxaldehyde-dimethylacetal.

The 5-oxides required as starting materials are produced as follows:

a. A solution of 60.0 g of 2-methylthio-5-phenyl-7-chloro-3H-1,4-benzodiazepine [cp. G. A. Archer et al., J.Org.Chem. 29, 231 (1964) ] and 38.8 g of diethoxyacetic acid hydrazide [produced by the storing of a mixture of 81.0 g of diethoxyacetic acid methyl ester, 50.0 g of hydrazine hydrate and 800 ml of abs. ethanol for 20 hours at 25°, filtration, concentration by evaporation of the filtrate and distillation of the residue in high vacuum, B.P. 120°–150°/0.005 Torr, M.P. 30°–40°] in 460 ml of abs. hexamethyl-phosphoric acid triamide is heated for 6 hours at 140°. The solvent is then distilled off in vacuo, and the residue distributed between methylene chloride and water. The organic phase is separated, washed with saturated sodium chloride solution, dried over sodium sulphate and concentrated by evaporation. The residue is recrystallised from ethyl acetate/ether/petroleum ether to obtain pure 6-phenyl-8-chloro-4H-s-triazolo[4,3-a][1,4]benzodiazepine-1-carboxaldehyde-diethylacetal, which melts at 133°–135°.

In an analogous manner there is obtained 6-phenyl-8-chloro-4H-s-triazolo[4,3-a][1,4]benzodiazepine-1-carboxaldehyde-dimethylacetal, M.P. 166°–172°, by the heating of 12.0 g of 2-methylthio-5-phenyl-7-chloro-3H-1,4-benzodiazepine with 7.0 g of dimethoxyacetic acid hydrazide (cp. E. J. Browns and J. B. Polya, J.Chem.Soc. 1962, 5149-5152) in 100 ml of abs. hexamethyl-phosphoric acid triamide for 9 hours at 140°.

b. A solution of 7.64 g (0.024 mole) of m-chloroperoxybenzoic acid in 140 ml of methylene chloride is added dropwise within 15 minutes at 0°–5°, with stirring, to a solution of 5.0 g (0.0126 mole) of 6-phenyl-8-chloro-4H-s-triazolo[4,3-a][1,4]benzodiazepine-1-carboxaldehyde-diethylacetal in 100 ml of methylene chloride. The reaction mixture is stirred for a further 16 hours in a melting ice bath. The reaction mixture is subsequently concentrated in vacuo and ether added. The precipitated crystals are filtered under suction and washed twice with hot ethyl acetate. The obtained 6-phenyl-8-chloro-4H-s-triazolo [4,3-a][1,4]benzodiazepine-1-carboxaldehyde-diethylacetal-5-oxide melts at 200°–202°.

There is obtained in an analogous manner, with the use of 4.65 g of 6-phenyl-8-chloro-4H-s-triazolo[4,3-a][1,4]benzodiazepine-1-carboxaldehyde-dimethylacetal:-6-phenyl-8-chloro-4H-s-triazolo[4,3-a][1,4]benzodiazepine-1-carboxaldehyde-dimethylacetal-5-oxide.

EXAMPLE 3

A solution of 1.0 g of 6-(o-chlorophenyl)-8-chloro-4H-s-triazolo[4,3-a][1,4]benzodiazepine-1-carboxaldehyde-diethylacetal in 100 ml of tetrahydrofuran is allowed to stand in a closed flask for 3 days in daylight. The solution is then concentrated in vacuo. The residue is adsorbed from benzolic solution on a column of silica gel, and eluted with a benzene/ethanol mixture (9:1, V/V). The fractions containing the desired reaction product (Rf-value = 0.73 in the system benzene/isopropanol 9:1) are combined and concentrated in vacuo. The residue is recrystallised from ethyl acetate/petroleum ether to obtain 10-chloro-11b-(o-chlorophenyl)-3,11bH-oxazirino [2,3-d]-s-triazolo[4,3-a][1,4]benzodiazepine-6-carboxaldehyde-diethyl acetal, M.P. 141°–142°.

The starting material is produced as follows:

a. 6-(o-Chlorophenyl)-8-chloro-4-H-s-triazolo[4,3-a][1,4]benzodiazepine-1-carboxaldehyde-diethylacetal, M.P. 120°–121.5°, is obtained by a 10-hours' heating of 16.7 g of 2-(methylthio)-5-(o-chlorophenyl)-7-chloro-3H-1,4-benzodiazepine [see note in Example 1 a)] and 9.7 g of diethoxyacetic acid hydrazide in 100 ml of hexamethyl-phosphoric acid triamide at 140°, processing analogous to that of Example 2 a) and subsequent recrystallisation from ethyl acetate/petroleum ether.

b. Analogously to Example 2 b) there is obtained, with the use of 5.44 g (0.0126 mole) of 6-(o-chlorophenyl)-8-chloro-4H-s-triazolo[4,3-a][1,4]benzodiazepine-1-carboxaldehyde-diethylacetal:- 6-(o-chlorophenyl)-8-chloro-4H-s-triazolo[4,3-a][1,4]benzodiazepine-1-carboxaldehyde-diethylacetal-5-oxide, which melts at 221°–222° after recrystallisation from ethyl acetate/petroleum ether.

EXAMPLE 4

A solution of 0.6 g of 6-phenyl-8-chloro-4H-s-triazolo[4,3-a][1,4]benzodiazepine-1-carboxaldehyde-diethylacetal-5-oxide in 60 ml of tetrahydrofuran is irradiated with a high-pressure mercury-discharge lamp through a Pyrex filter for 2 hours at 25°. The solution is afterwards concentrated to 20 ml and petroleum ether added. 10-Chloro-11b-phenyl-3,11bH-oxazirino[2,3-d]-s-triazolo[4,3-a][1,4]benzodiazepine-6-carboxaldehyde-diethylacetal crystallises out and is filtered off, M.P. 136°–137°.

What we claim is:

1. A diazepine derivative having the formula I

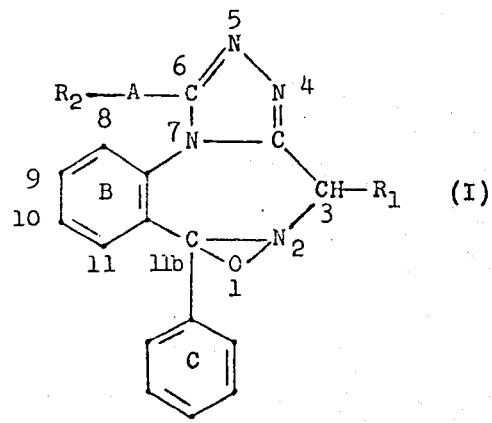

wherein
$R_1$ represents hydrogen or an alkyl group having 1 to 3 carbon atoms,
A represents an alkylene group having 1 to 3 carbon atoms,
$R_2$ represents a hydroxyl group, benzyloxy, o-, m- or p-chlorobenzyloxy o-, m- or p-methylbenzyloxy, o-, m- or p-methoxybenzyloxy, or diphenylmethoxy group, or
$R_2$—A together represent a dialkoxymethyl group of which the alkoxy radicals contain 1 to 4 carbon atoms, and
each of the rings B and C, independently of the other, is unsubstituted or mono-substituted by halogen up to atomic number 35, trifluoromethyl, alkyl or alkoxy groups having 1 to 6 carbon atoms.

2. A compound according to claim 1, having the formula I given in claim 1 wherein $R_1$ represents hydrogen, $R_2$ represents the hydroxyl, benzyloxy or p-methoxybenzyloxy group, A represents the methylene group, ring B is substituted in the 10-position by chlorine, and ring C is unsubstituted or substituted in the o-position by fluorine or chlorine.

3. A compound according to claim 1 having the formula I given in claim 1, wherein $R_1$ represents hydrogen, $R_2$—A together represent the dimethoxymethyl or diethoxymethyl group, ring B is substituted in the 10-position by chlorine, and ring C is unsubstituted or substituted in the o-position by fluorine or chlorine.

4. A compound according to claim 1, which is 10-chloro-11b-phenyl-3,11bH-oxazirino[2,3-d]-s-triazolo[4,3-a][1,4]benzodiazepine-6-methanol.

5. A compound according to claim 1 which is 10-chloro-11b-phenyl-3,11bH-oxazirino[2,3-d]-s-triazolo[4,3-a][1,4]benzodiazepine-6carboxaldehyde-diethylacetal.

6. A compound according to Claim 1, which is 10-chloro-11b-(o-chlorophenyl)-3,11bH-oxazirino[2,3-d]-s-triazolo[4,3-a][1,4]benzodiazepine-6-carboxaldehyde-diethylacetal.

* * * * *